(12) United States Patent
Cerofolini (10) Patent No.: US 8,439,841 B2
(45) Date of Patent: May 14, 2013

(54) METHOD OF MEASURING THE THICKNESS OF A BIOLOGICAL TISSUE BY ULTRASOUNDS AND DEVICE FOR CARRYING OUT SUCH METHOD

(75) Inventor: Marino Cerofolini, Subbiano (IT)

(73) Assignee: Esaote S.p.A., Milan (IT)

( * ) Notice: Subject to any disclaimer, the term of this patent is extended or adjusted under 35 U.S.C. 154(b) by 150 days.

(21) Appl. No.: 13/083,141

(22) Filed: Apr. 8, 2011

(65) Prior Publication Data

US 2011/0257531 A1 Oct. 20, 2011

(30) Foreign Application Priority Data

Apr. 14, 2010 (IT) .............................. GE2010A0035

(51) Int. Cl.
*A61B 8/00* (2006.01)

(52) U.S. Cl.
USPC ........... 600/449; 600/444; 600/445; 600/437; 600/459

(58) Field of Classification Search .................. 600/449, 600/443–445, 437, 459
See application file for complete search history.

(56) References Cited

U.S. PATENT DOCUMENTS

| 5,050,128 | A | * | 9/1991 | Saitoh et al. ....................... 367/7 |
| 5,381,794 | A | | 1/1995 | Tei et al. |
| 5,740,804 | A | | 4/1998 | Cerofolini |
| 5,941,825 | A | * | 8/1999 | Lang et al. .................... 600/449 |
| 2005/0124889 | A1 | | 6/2005 | Flesch |
| 2006/0241452 | A1 | | 10/2006 | Cerofolini |
| 2010/0218590 | A1 | | 9/2010 | Foisy |

FOREIGN PATENT DOCUMENTS

| JP | 60181606 | 9/1985 |
| WO | 2009080562 | 7/2009 |
| WO | 2010075553 | 7/2010 |

* cited by examiner

*Primary Examiner* — Long V. Le
*Assistant Examiner* — Farshad Negarestan
(74) *Attorney, Agent, or Firm* — Themis Law (57) ABSTRACT

A method of measuring the thickness of a biological tissue by ultrasounds and a device carrying out such method. The method is implemented with an ultrasound probe that emits ultrasonic pulses within a body under examination and receives echoes generated from structures of the body under examination. The probe includes an array of two or more electro-acoustic transducers and, in combination, means for processing the reception signals and means for orienting one or more lines of sight, along which the emission of the pulses and/or the reception of the echoes is focused, according to different angles with respect to an axis perpendicular to the emitting surface of the probe. The thickness of the biological tissue is calculated by the time interval between the reception of the first echo and the reception of the second echo, which are relevant to the same ultrasonic pulse emitted along at least a line of sight oriented along an axis perpendicular to the surface of the biological tissue, which is defined by the iteration of measurements with the line of sight oriented at different angles and with comparisons between the measured intensity values, the orientation corresponding to the axis perpendicular to the surface of the biological tissue being the one showing the maximum intensity of the first echo.

8 Claims, 6 Drawing Sheets

METHOD OF MEASURING THE THICKNESS OF A BIOLOGICAL TISSUE BY ULTRASOUNDS AND DEVICE FOR CARRYING OUT SUCH METHOD

FIELD OF THE INVENTION

The present invention relates to a method of measuring the thickness of a biological tissue by ultrasounds and to a device for carrying out such method.

The method is carried out by an ultrasound probe which emits ultrasonic pulses within a body under examination and receives echoes generated from structures of the body under examination, and which includes an array of two or more electro-acoustic transducers and, in combination, means that process the reception signals and with means that orient one or more lines of sight, along which the emission of the pulses and/or the reception of the echoes is focused, according to different angles with respect to an axis perpendicular to the emitting surface of the probe.

The present invention further relates to a device which measures the thickness of a biological tissue by ultrasounds, and which comprises:

a probe having an array of electro-acoustic transducers configured to emit ultrasonic pulses within a body under examination and an array of electro-acoustic transducers configured to receive the echoes generated from structures of the body under examination, means that process the reception signals, and means that orient one or more lines of sight, along which the emission of the pulses and/or the reception of the echoes is focused, according to different angles with respect to an axis perpendicular to the emitting surface of the probe.

The method and the device of the present invention can be used to measure the thickness of any biological tissue, both in vivo and in vitro, but are particularly advantageously used to measure the thickness of the skin.

BACKGROUND OF THE INVENTION

In recent years, measuring the thickness of the skin has played an increasingly important role in the medical field, since experimental evidence has shown a correlation between abnormal values of the skin thickness and several diseases or disorders.

In particular, a skin thickness exceeding reference values is confirmed to be correlated with rheumatic diseases such as, for example, sclerodermia.

Moreover, a correlation between skin thickness and mutations in the GJB2 gene has been found, which is in turn correlated to hearing loss, as shown in document WO 2009/08056A2.

The use of ultrasounds for measuring skin thickness is known and is fraught with technical difficulties mainly due to two aspects.

The first aspect relates to the deformability of the skin under the pressure of an ultrasound probe, which can cause the skin under examination to be locally compressed, thus resulting in underestimated values or more generally in values different than the real value.

The second aspect relates to the measurement being taken along an axis perpendicular to the skin surface to achieve a real evaluation, since a measurement taken along axes inclined at angles different than the axis perpendicular to the skin surface may result in overestimated values or again generally in values different than the real value.

The same considerations are to be considered as valid even when the object to be measured is a biological tissue different than the skin.

Known methods and devices, such as for example those described in the above mentioned document WO 2009/08056A2, do not completely solve the above mentioned drawbacks, because they try reaching a compromise between the minimum compression of the skin on the one hand and the orthogonality between probe and skin on the other hand, by means of optical and inclinometric sensors that considerably increase hardware complexity and the computational burden affecting software components without guaranteeing optimal results.

SUMMARY OF THE INVENTION

The aim of the present invention is to overcome the drawbacks related to the prior art by a method having the features defined hereinbefore, and wherein, in addition, the thickness of the biological tissue is calculated by the time interval between reception of the first echo and reception of the second echo, which are relevant to the same ultrasonic pulse that is emitted along at least a line of sight oriented along an axis perpendicular to the surface of the biological tissue, and wherein the axis perpendicular to the surface of the biological tissue is defined by sequentially orienting the line of sight according to different angles using orienting means.

For each angle the intensity of the first received echo is measured such that by the iteration of measurements according to different angles and by comparisons of the measured intensity values the orientation of the line of sight having the maximum intensity of the first echo is defined, such orientation corresponding to the axis perpendicular to the surface of the biological tissue.

Thus, the great advantage is achieved of iteratively orienting the line of sight according to different angles with respect to an axis perpendicular to the emitting surface, which generally is coincident with the longitudinal axis of the probe, till an orientation is found coinciding with the axis perpendicular to the surface of the biological tissue, along which a real measurement of the thickness of the biological tissue can be taken.

This means that even if the probe is not perfectly perpendicular to the surface of the biological tissue, or more generally if the emitting surface of the probe is not perfectly parallel to the surface of the biological tissue, the measurement is taken anyway along an axis perpendicular to the surface of the biological tissue.

In a preferred embodiment, the method of the present invention includes the following steps:

(a) orienting the line of sight according to an axis perpendicular to the emitting surface of the probe, emitting the pulse and receiving echoes;

(b) measuring Vo which is defined as the intensity value of the first detected echo with the orientation defined at step a;

(c) orienting the line of sight along a first plane passing through the axis perpendicular to the emitting surface of the probe by a predetermined angle with respect to the axis, emitting the pulse and receiving echoes;

(d) measuring V1 which is defined as the intensity value of the first detected echo with the orientation defined at step c;

(e) comparing V0 and V1, if V0>V1 orienting the line of sight within the first plane by an angle greater than the orientation defined at step (c), emitting the pulse and receiving echoes, if V0<V1 orienting the line of sight within the first plane by an angle corresponding to the one defined at step (c) but in a direction symmetric with respect to the axis perpendicular to the emitting surface of the probe, emitting the pulse and receiving echoes;

(f) iterating steps (b), (c), and (d) with the line of sight oriented according to angles that are progressively greater within the first plane;

(g) defining the orientation of the line of sight with an angle corresponding to a maximum value measured on the first plane, which is defined as the measured value greater than the value measured at the previous iteration step and than the value measured at the subsequent iteration step;

(h) iterating steps (a) to (g), starting from the line of sight oriented as defined at step (g) and with subsequent orientations along a second plane not coinciding with the first plane and passing through such line of sight, till the axis perpendicular to the plane of the biological tissue is found, which is defined as the orientation corresponding to a maximum value measured within the second plane.

Starting from the line of sight oriented along the axis perpendicular to the emitting surface of the probe, and that is generally the longitudinal axis of the probe, the aim is to find the maximum value of the first echo according to subsequent orientations by increasing from time to time the angle of the line of sight while keeping it on a single first plane.

The second orientation of the line of sight, immediately following the initial step corresponding to the line of sight oriented along the axis perpendicular to the emitting surface of the probe, is carried out in an arbitrary direction, that is in any of the two half planes defined by the axis perpendicular to the emitting surface of the probe and lying opposite each other on the first plane.

The maximum value on such first plane corresponds to an orientation having a value greater than the angle corresponding to the subsequent acquisition step, and than the angle corresponding to the previous acquisition step.

To this end, the value acquired at the second-last step on such first plane is defined as the maximum value on such first plane if the value detected at the last step is smaller than that acquired at the second-last step, that is, at the immediately previous step.

In the particular case where in the second step, immediately following the initial step corresponding to the line of sight being oriented along the axis perpendicular to the emitting surface of the probe, a value smaller than that of the initial step is detected, the line of sight is oriented by the same angle but it is arranged symmetrically with respect to the axis perpendicular to the emitting surface of the probe, that is in the opposite half-plane, and if necessary, further orientations with greater and greater angles shall lie on such half plane.

Once the maximum value has been found in the first plane, a second plane different than the first one is defined which passes through the orientation of the line of sight corresponding to such maximum value in the first plane, and the process is repeated in order to find the maximum value even on the second plane, corresponding to the maximum value on the whole volume insonificated by the probe, if assuming the biological tissue to be substantially flat in the area under examination.

As the maximum value of the first echo corresponds to the point showing the smallest distance between the surface plane of the biological tissue and the point of origin of the lines of sight, such point is necessarily arranged along the axis perpendicular to the surface of the biological tissue passing through the point of origin of the lines of sight.

This method provides for the smallest number of orientation steps for aligning the line of sight along an axis perpendicular to the surface of the biological tissue, thus considerably reducing time and the computational burden.

In a further particularly advantageous embodiment, above all as regards the realization of a device intended to carry out the method, the first plane and the second plane are perpendicular to each other.

In an advantageous embodiment the line of sight is oriented with different angles by a regular sequential increase in the angle between the line of sight and the axis perpendicular to the emitting surface of the probe, the increase ranging from 0.5 to 4 degrees, preferably from 1 to 3 degrees and particularly being 2 degrees.

The orienting means for one or more lines of sight can comprise in combination or alternatively with one another:

an electronic unit managing the delays to be applied to the emission and/or reception of electro-acoustic transducers for adjusting the steering angle of the beam emitted by the probe;

mechanical means for oscillating the array of transducers about at least an axis parallel to the emitting surface of the probe and/or passing therethrough;

manually oscillating the array of transducers and/or the entire probe about at least an axis parallel to the emitting surface of the probe and/or passing therethrough.

Each of the above mentioned oscillating modes for orienting the line of sight may be provided along at least a plane perpendicular to the emitting surface of the probe, both independently and in combination with the other modes. For example by using a linear probe with an array of transducers oscillating about an axis parallel to the longitudinal extension of the linear array of transducers, it is possible to adjust the inclination of the ultrasound beam emitted in the plane parallel to the longitudinal axis of the transducer array by electronic steering acting on the beamforming delays of the beam, while in the plane perpendicular to the longitudinal extension of the transducer array the inclination is adjusted by oscillating with predetermined steps the transducer array about the axis parallel to the longitudinal axis of the transducer array.

In a particular embodiment, the probe is provided with an enlargement of the probe surface at the emitting side by means of a frame which surrounds the array of electro-acoustic transducers and it projects in the emitting direction of the transducers having a surface resting on the body under examination, an acoustic matching layer being interposed between the electro-acoustic transducers and the body under examination.

In a further embodiment, the method is carried out by emitting radio frequency ultrasonic pulses.

The present invention relates also to a device for measuring the thickness of a biological tissue by ultrasounds with the characteristics described hereinbefore, which device provides also an enlargement of the probe surface at the emitting side by means of a frame which surrounds the array of electro-acoustic transducers and it projects in the emitting direction of the transducers having a surface resting on the body under examination, an acoustic matching layer being interposed between the electro-acoustic transducers and the body under examination in the area defined by the frame.

The enlargement allows the pressure of the probe on the biological tissue to be distributed on a large surface, thus locally decreasing its value and therefore avoiding a reduction due to the compression effect.

The frame arrangement allows also the pressure to be distributed only along the edges of the enlargement and, therefore, allows the biological tissue in the area within the frame, which is the emitting area of the electro-acoustic transducers, not to be affected by the compression effect.

In one embodiment, the contact surface between the frame and the body under examination is at least partially covered by a layer made of elastomeric material.

By means of such characteristic the pressure of the probe on the biological tissue/skin is further reduced on the whole contact surface.

In a preferred embodiment, the acoustic matching layer is made of a gelatinous material, in particular anechoic material.

By means of this arrangement, the first reflected signal is guaranteed to come from the surface of the skin and not from reflections inside the material, which otherwise would make it difficult to define the exact time when the acoustic pulse impinges on the skin surface and consequently, would make it difficult to measure skin thickness.

In a further embodiment, between the frame and the matching layer there is also provided a gap allowing the acoustic matching layer and/or the elastomeric layer to expand transversally to the emitting direction during the examination.

The electro-acoustic transducers can be arranged as a two-dimensional array or as a linear assembly so called linear array (a row of transducers placed side by side along an axis), such that the emission of ultrasonic pulses can be focused along at least a line of sight.

The means for orienting the line of sight can comprise in combination or alternatively with one another:

an electronic unit managing the delays to be applied to the emission and/or reception of electro-acoustic transducers;

mechanical means for oscillating the array of transducers about at least an axis parallel to the emitting surface of the probe and/or passing therethrough;

manually oscillating the array of transducers and/or the entire probe about at least an axis parallel to the emitting surface of the probe and/or passing therethrough.

It is possible to provide each of the above mentioned oscillating modes for orienting the line of sight along at least a plane perpendicular to the emitting surface of the probe, both independently and in combination with each other.

In particular, by combining the above mentioned features it is possible to obtain two alternative and particularly advantageous embodiments.

In a first embodiment, the array of electro-acoustic transducers is arranged as a two-dimensional array and the line of sight is oriented on the first plane and on the second plane by means of the electronic unit managing the delays to be applied to the emission and/or reception of the electro-acoustic transducers.

In a second embodiment, the array of electro-acoustic transducers is arranged as a linear array and the line of sight is oriented on the first plane by means of the electronic unit managing the delays to be applied to the emission and/or reception of the electro-acoustic transducers and on the second plane by means of the mechanical means for oscillating the array of transducers about at least an axis parallel to the emitting surface of the probe and/or passing therethrough.

In particular, such means can provide the array of transducers to be fitted so as to oscillate about an axis parallel to the emitting surface of the probe and the oscillation to be operated by a motor, preferably an electric motor, connected to the transducer array.

In a preferred embodiment, the probe emits radio frequency ultrasonic pulses.

BRIEF DESCRIPTION OF THE DRAWINGS

These and other characteristics and advantages of the present invention will be clearer from the following description of some embodiments shown in the enclosed drawings, wherein.

DETAILED DESCRIPTION OF EMBODIMENTS OF THE INVENTION

Figure 1:
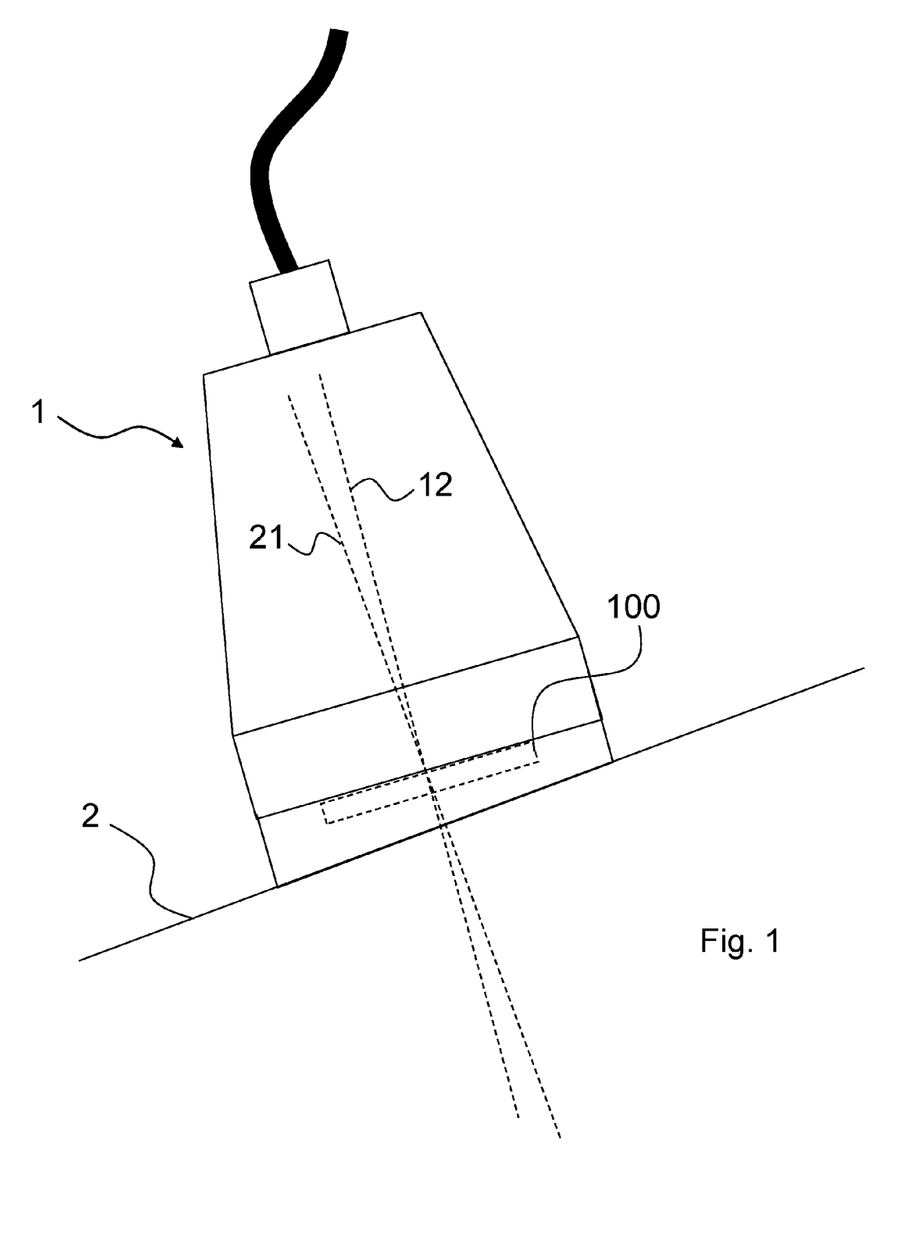
FIG. 1 is the probe of the present invention placed on the biological tissue under examination according to such an orientation that the axis perpendicular to the emitting surface of the probe does not coincide with the axis perpendicular to the surface of the biological tissue.

FIG. 1 shows the probe 1 of the present invention, which includes an array of electro-acoustic transducers 100 defining an emitting surface, and which is placed on the biological tissue 2 under examination according to an inclination such that the axis perpendicular to the emitting surface of the probe 12 does not perfectly coincide with the axis perpendicular to the surface of the biological tissue 21.

In this event the measurement of the thickness of the biological tissue 2 according to a line of sight oriented along the axis perpendicular to the emitting surface of the probe 12 does not result in the real value of the thickness.

In order to obtain the real value of the thickness of the biological tissue 2, the present invention provides a method which is carried out by an ultrasound probe 1 that emits ultrasonic pulses within a body under examination and that receives echoes generated from structures of the body under examination. The probe comprises an array 100 of two or more electro-acoustic transducers and is provided in combination with means for processing the reception signals and with means for orienting one or more lines of sight, along which the emission of the pulses and/or the reception of the echoes is focused, according to different angles with respect to the axis perpendicular to the emitting surface of the probe 12.

The thickness of the biological tissue 2 is calculated by the time interval between the reception of the first echo and the reception of the second echo, which are relevant to the same ultrasonic pulse emitted along a line of sight oriented along the axis perpendicular to the surface of the biological tissue 21, the axis perpendicular to the surface of the biological tissue being defined by sequentially orienting the line of sight according to different angles, by means of the orienting means.

For each angle, the intensity of the first received echo is measured such that by the iteration of measurements according to different angles and by comparisons of the measured intensity values the orientation of the line of sight having the maximum intensity of the first echo is defined, such orientation corresponding to the axis perpendicular to the surface of the biological tissue 21.

Figure 2:
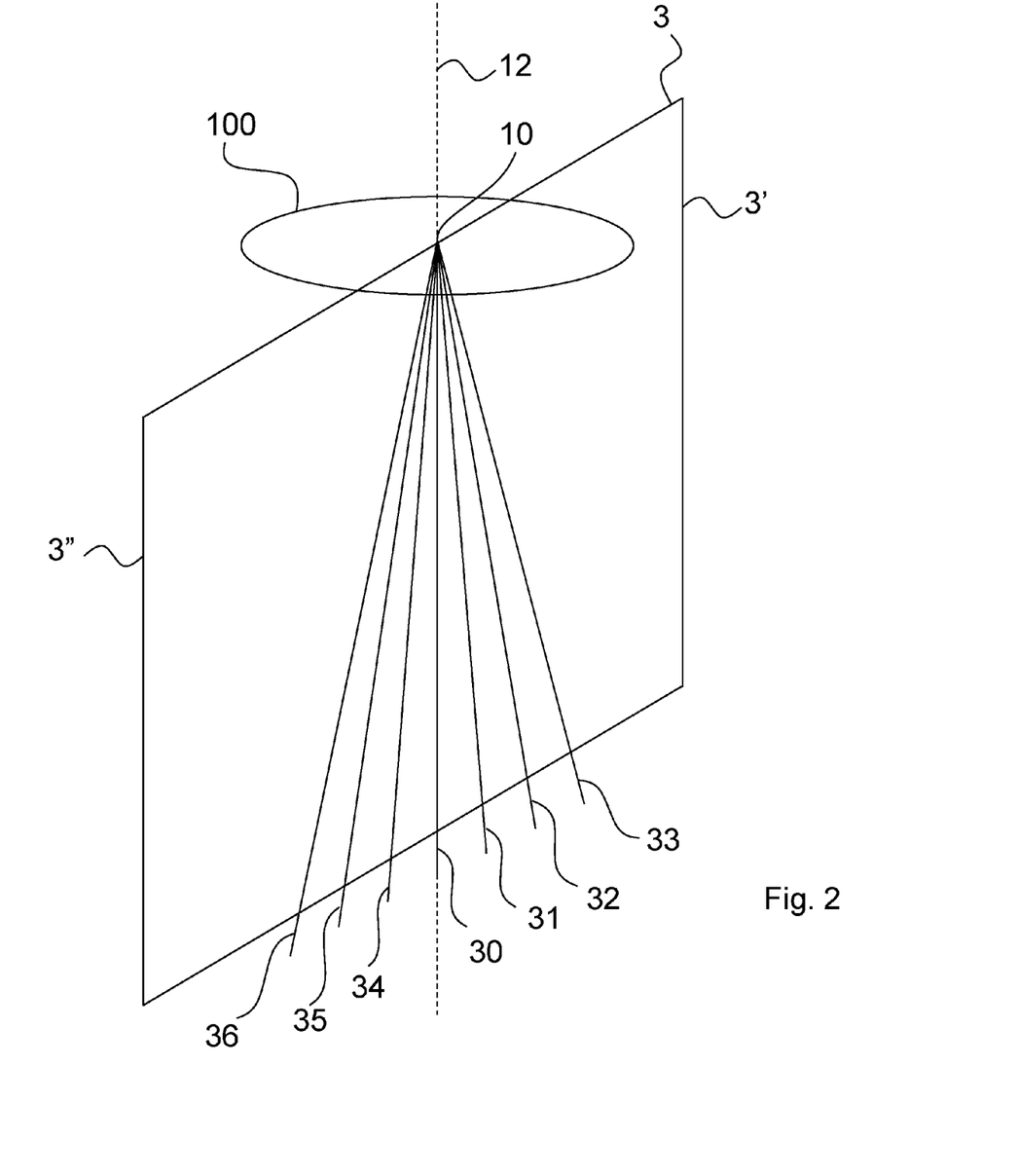
FIGS. 2, 3 and 4 schematically show the subsequent steps of the method of the present invention.
Figure 3:
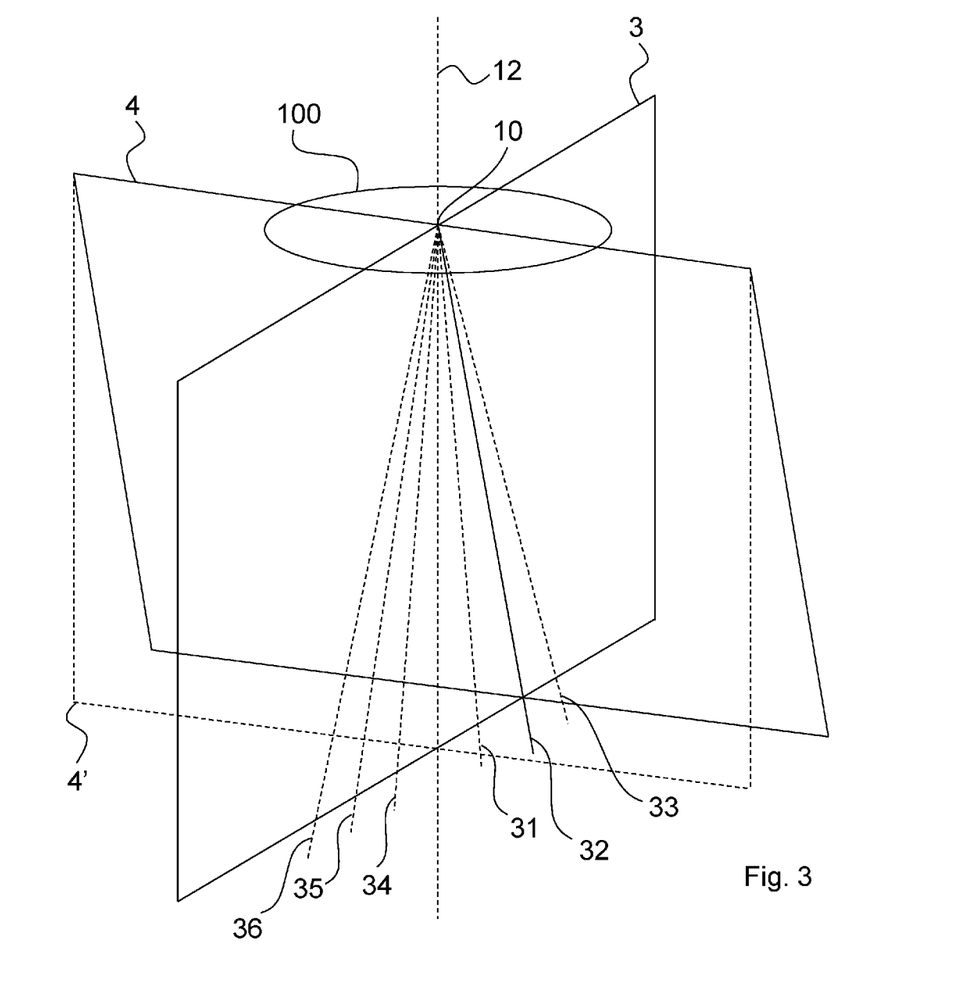
Figure 4:
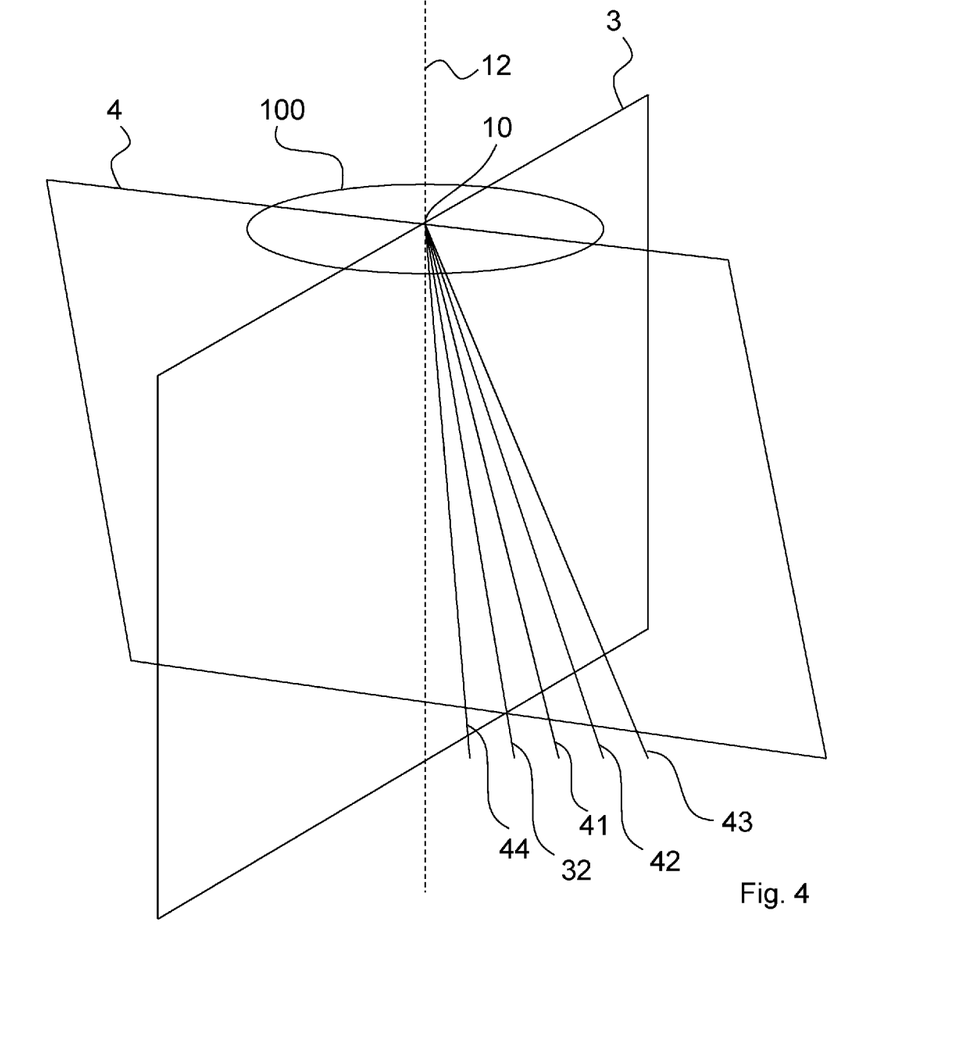

Such method is schematically shown in FIGS. 2, 3 and 4, in which the array of transducers 100 is shown as being generally, but not limited to, a circular one.

The transducer array 100 can have any shape and arrangement, particularly forming a two-dimensional array or a linear array.

In order to carry out the method of the present invention, as it can be clearly seen in FIG. 2, starting from an orientation 30 of the line of sight along the axis perpendicular to the emitting surface of the probe 21, and that is, generally the longitudinal axis of the probe 1, the aim is to find the maximum value of the first echo according to subsequent orientations 31, 32, 33 by increasing from time to time the angle of the line of sight but keeping it on a single first plane 3.

The second orientation 31 of the line of sight, immediately following the initial orientation 30 along the axis perpendicular to the emitting surface 12 of the probe, is made in an arbitrary direction, that is, in any of the two half-planes 3' and 3" defined by the axis perpendicular to the emitting surface 12 of the probe and lying opposite each other on the first plane 3, particularly in FIG. 2 in the half plane 3'.

The maximum value on such first plane 3 corresponds to an orientation having a value greater than the angle corresponding to the subsequent acquisition step, and than the angle corresponding to the previous acquisition step.

To this end, the value acquired at the second-last step on such first plane 3 is defined as the maximum value on such first plane 3 if the value detected at the last step is smaller than that acquired at the second-last step, that is, at the immediately previous step.

In the particular case where in the second orientation 31, immediately following the initial orientation 30 corresponding to the axis perpendicular to the emitting surface 12 of the probe, a value smaller than the one according to the initial orientation 30 is detected, the orientation 34 of the line of sight is performed with the same angle but it is symmetrically arranged with respect to the axis perpendicular to the emitting surface of the probe, that is, in the opposite half-plane 3", and the further orientations 36, 36 etc, at greater and greater angles will be on such half-plane 3" if necessary.

Once the maximum value has been found in the first plane 3, assuming such maximum value to correspond to the orientation 32 as in FIG. 3, a second plane 4 different than the first one is defined passing through the orientation 32 of the line of sight corresponding to such maximum value in the first plane 3, and the process is repeated in order to find the maximum value even on the second plane 4, corresponding to the maximum value on the whole volume insonificated by the probe, if assuming the biological tissue to be substantially flat in the area under examination.

Preferably the first plane 3 and the second plane 4 are perpendicular to each other.

In order to point out that the second plane 4 is perpendicular to the first plane 3 but passing through the orientation 32 of the line of sight corresponding to the maximum value on the plane 3, in FIG. 3 the plane 4' perpendicular to the first plane 3 and passing through the axis perpendicular to the emitting surface 12 of the probe has been shown with a broken line.

As the maximum value of the first echo corresponds to the point showing the smallest distance between the surface plane of the biological tissue 2 and the point of origin 10 of the lines of sight, such point is necessarily arranged along the axis perpendicular to the surface of the biological tissue passing through the point of origin of the lines of sight 10.

In an advantageous embodiment the orientations of the lines of sight at different angles are obtained by a sequential regular increase in the angle between the line of sight and the axis perpendicular to the emitting surface 12 of the probe, the increase ranging from 0.5 to 4 degrees, preferably from 1 to 3 degrees and particularly being 2 degrees.

FIGS. 5a, 5b, 6a and 6b show different views of two preferred embodiments of the device of the present invention.

The device comprises a probe 1 having an array 100 of electro-acoustic transducers for emitting ultrasonic pulses into a body under examination and an array of electro-acoustic transducers for receiving echoes generated by structures of the body under examination, means for processing the reception signals and means for orienting one or more lines of sight, along which the emission of the pulses and/or the reception of the echoes is focused, according to different angles with respect to an axis perpendicular to the emitting surface of the probe.

Advantageously, the same transducers can be used both for the emission and the reception.

The device of the present invention further provides an enlargement of the probe surface at the emitting side by means of a frame 103 which surrounds the array 100 of electro-acoustic transducers and it projects in the emitting direction of the transducers having a surface resting on the body under examination, an acoustic matching layer 102 being interposed between the electro-acoustic transducers and the body under examination in the gap delimited by the frame.

The surface of the frame 103 in contact with the body under examination is at least partially covered with a layer 101 made of elastomeric material and the acoustic matching layer 102 is made of a gelatinous material, particularly anechoic material.

Figure 5A:
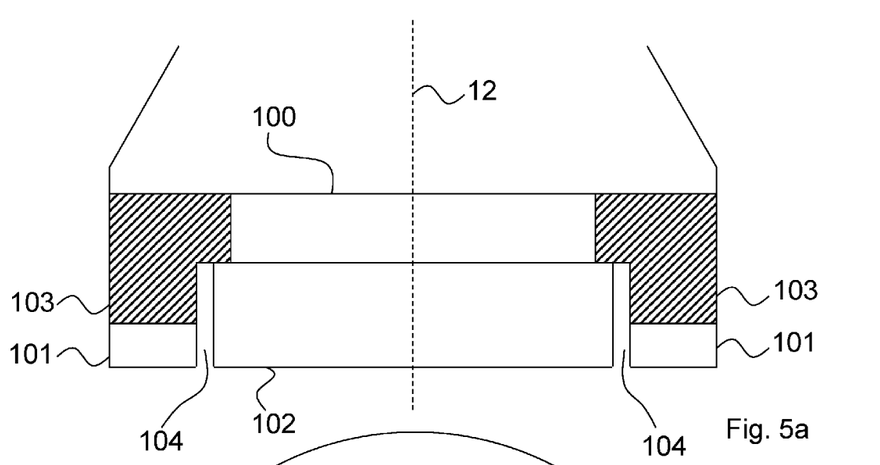
FIGS. 5a and 5b are a longitudinal section and a view taken from the emitting side of the probe head respectively in a first embodiment.
Figure 5B:
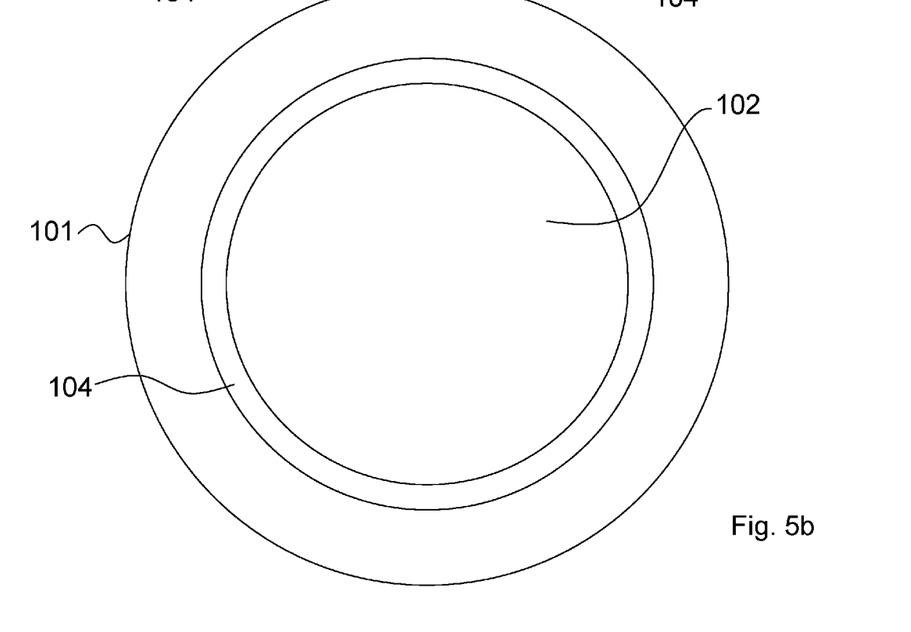

In FIGS. 5a and 5b the probe head has a circular section and the array 100 of electro-acoustic transducers is arranged according to a two-dimensional array such that the line of sight can be oriented both on the first plane 3 and on the second plane 4 by an electronic unit managing the delays to be applied to the emission and/or reception of the electro-acoustic transducers.

The transducer assembly 100 arranged as an array is surrounded by a circular crown-like frame 103 projecting in the emitting direction of the probe 1, having a layer of elastomeric material 101 in the contact area.

The acoustic matching layer 102 made of anechoic gelatinous material is in contact with the array of transducers 100, on the emitting side thereof.

The frame 103 and the acoustic matching layer 102 have such a shape that they have resting surfaces that are substantially on the same plane in order to be uniformly placed on the surface of the tissue 2 under examination.

Moreover between the frame 103 and the acoustic matching layer 102 there is provided a gap 104 intended to allow the acoustic matching layer 102 and/or the layer 101 made of elastomeric material to expand transversely to the emitting direction during the examination process if necessary.

Figure 6A:
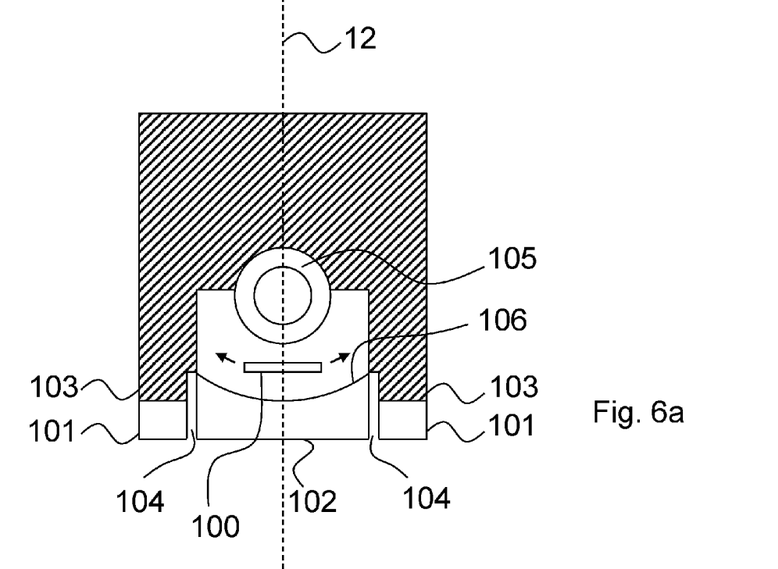
FIGS. 6a and 6b are a longitudinal section and a view taken from the emitting side of the probe head respectively in a second embodiment.
Figure 6B:
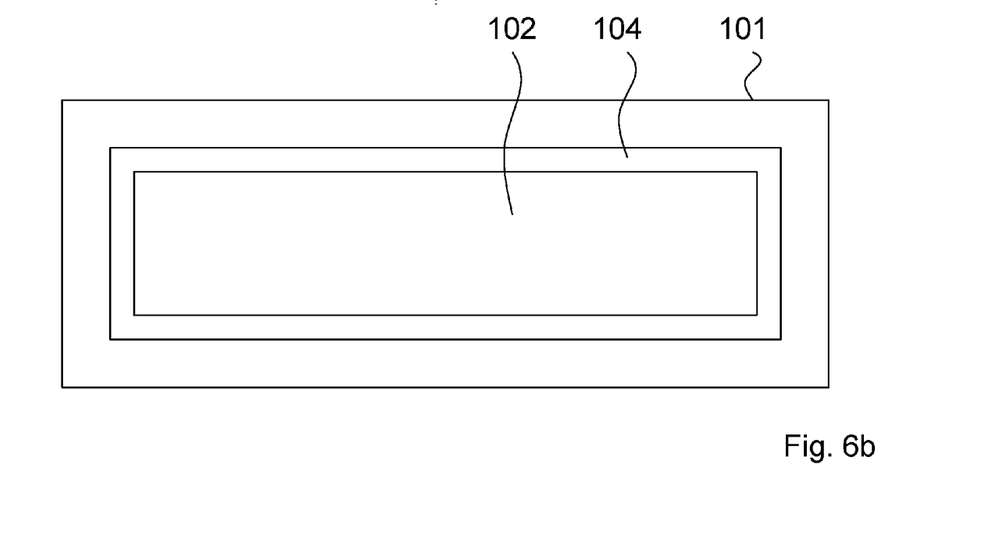

FIGS. 6a and 6b show a second preferred embodiment, which provides for the array 100 of electro-acoustic transducers to be arranged as a linear array and the line of sight to be oriented on the first plane 3 by means of the electronic unit managing the delays to be applied to the emission and/or reception of the electro-acoustic transducers and on the second plane 4 by means of the mechanical means oscillating the transducer array about at least an axis parallel to the emitting surface of the probe and/or passing therethrough.

In particular such means provide the transducer array to be fitted so as to oscillate about an axis parallel to the emitting surface of the probe and the oscillation to be driven by a motor 105, preferably an electric motor, connected to the transducer array.

In the embodiment shown in the figure, the axis parallel to the emitting surface of the probe passes through the motor 105, such that the transducer array 100 oscillates in the directions shown by the arrows.

The transducer array 100 is housed so as to oscillate into a cavity delimited at the emitting side by a sealing curved diaphragm 106 and filled with acoustic matching liquid.

These types of probes are known both in combination with linear arrays and with two-dimensional arrays. Moreover probes are also known wherein the transducer array can be oscillated by means of motors according to two axes perpendicular to each other and perpendicular to the direction of propagation of the ultrasound beam, that is the longitudinal axis of the probe or according to two axes perpendicular to each other and lying in the plane parallel to or tangent to the plane subtended by the transducer array. Constructional examples of such probes are shown and described in documents EP 1167996 and EP 1681020 to the same applicant. Such descriptions are incorporated herein by reference.

The description related to FIGS. 5a and 5b is valid even for this embodiment, except for the means oscillating the transducer array 100 and for the substantially rectangular section of the head of the probe 1.

In a preferred embodiment, the probe 1 emits radio frequency ultrasonic pulses.

The detected thickness values can be displayed in the numerical or visual format or in the combined format. Particularly it is possible to display the measured thickness as visual information which is numerically represented into a window adjacent to or superimposed on a conventional B mode image. The B-mode image can be acquired in parallel to or alternatively to the thickness measurement by means of the same ultrasound probe.

It is also possible to display within the B-mode image a line showing the line of sight defined by the system according to the invention and along which the thickness has been measured while showing on the same line the starting point and the end point of the segment of the measured thickness and placed on the B-mode image. Thus it is possible to immediately see the point where the thickness has been measured with reference to the field of view of the probe, the direction of the straight line along which such measurement has been taken and the segment of the straight line with the measured length and in registration with the B-mode image. This allows the reliability of the measurement to be immediately verified as regards the above mentioned parameters automatically defined by the system according to the invention.

It is also possible to take measurements of the thickness by translating the probe in order to acquire the thickness at different locations within an anatomical district to be examined and therefore in order to display the thickness data as an image.

As regards data to be displayed, any current modes may be used in displaying data acquired by an ultrasound examination.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

The invention claimed is:

1. A method of measuring a thickness of a biological tissue by ultrasounds comprising:
    emitting ultrasonic pulses within a body under examination and receiving echoes generated from structures of said body under examination by an ultrasound probe comprising an array of two or more electro-acoustic transducers, said probe being configured to process reception signals and to orient one or more lines of sight, along which emission of said pulses or reception of said echoes is focused, according to different angles with respect to an axis perpendicular to an emitting surface of said probe; and
    calculating the thickness of said biological tissue by a time between reception of a first echo and reception of a second echo, which are relevant to a same ultrasonic pulse emitted along at least a line of sight oriented along an axis perpendicular to a surface of the biological tissue, said axis perpendicular to the surface of the biological tissue being defined by sequentially orienting the line of sight according to different angles, using said probe, by the following steps:
    (a) orienting a line of sight according to an axis perpendicular to the emitting surface of the probe, and emitting the pulses and receiving the echoes along the line of sight;
    (b) measuring $V_0$, which is defined as intensity value of a first detected echo with the orienting defined at step (a);
    (c) orienting the line of sight along a first plane passing through said axis perpendicular to the emitting surface of the probe by a predetermined angle with respect to said axis, and emitting the pulses and receiving the echoes along the line of sight;
    (d) measuring $V_1$, which is defined as the intensity value of the first detected echo with the orientation defined at step (c);
    (e) comparing $V_0$ and $V_1$, if $V_1 > V_0$ orienting the line of sight within said first plane by an angle greater than the orientation defined at step (c) and emitting the pulses and receiving the echoes along the line of sight, and if $V_1 < V_0$ orienting the line of sight within said first plane by an angle corresponding to the angle defined at step (c) but in a direction symmetric with respect to the axis perpendicular to the emitting surface of the probe and emitting the pulses and receiving echoes along the line of sight;
    (f) iterating steps of measuring the intensity value along the line of sight, comparing the measured intensity value with a previously measured intensity value, and orienting the line of sight according to angles that are progressively greater within said first plane;
    (g) defining the orientation of the line of sight with an angle corresponding to a maximum intensity value measured on said first plane, which is defined as a measured value greater than a value measured at a previous iteration step and than a value measured at a subsequent iteration step; and
    (h) iterating steps (a) to (g), starting from the line of sight oriented as defined at step (g) and with subsequent orientations along a second plane not coinciding with the first plane and passing through the line of sight with maximum intensity value, until the axis perpendicular to the plane of the biological tissue is determined as the orientation corresponding to a maximum value measured within the second plane.

2. The method according to one claim 1, wherein said first plane and said second plane are perpendicular to each other.

3. The method according to claim 1, wherein the line of sight is oriented according to the different angles by a regular sequential increase in an angle formed between the line of sight and the axis perpendicular to the emitting surface of the probe, said increase ranging from 0.5 to 4 degrees.

4. The method according to claim 1, wherein the the probe is configured to orient the one or more lines of sight by having an electronic unit managing delays to be applied to one or more of the emission or reception of electro-acoustic transducers for orienting the lines of sight along at least a plane perpendicular to the emitting surface of the probe.

5. The method according to claim 1, wherein the probe is configured to orient the one or more lines of sight by mechanically oscillating the array of transducers about at least an axis parallel to the emitting surface of the probe or passing therethrough for orienting the lines of sight along at least a plane perpendicular to the emitting surface of the probe.

6. The method according to claim 1, wherein the probe is configured to orient the one or more lines of sight by manually causing the array of transducers or the entire probe to oscillate about at least an axis parallel to the emitting surface of the probe or passing therethrough for orienting the lines of sight along at least a plane perpendicular to the emitting surface of the probe.

7. The method according to claim 1, wherein the emitting surface of the probe is provided with an enlargement by a frame which surrounds the array of electro-acoustic transducers and projects in an emitting direction of the transducers, having a surface resting on the body under examination, an acoustic matching layer being interposed between the electro-acoustic transducers and the body under examination.

8. The method according to claim 1, wherein radio frequency ultrasonic pulses are emitted.

\* \* \* \* \*